(12) United States Patent
Miller et al.

(10) Patent No.: US 7,658,718 B2
(45) Date of Patent: *Feb. 9, 2010

(54) BIOPSY NEEDLE WITH INTEGRATED GUIDE PIN

(75) Inventors: Michael E. Miller, Trafalgar, IN (US); Dan C. Ireland, Martinsville, IN (US)

(73) Assignee: Promex Technologies, LLC, Franklin, IN (US)

( * ) Notice: Subject to any disclaimer, the term of this patent is extended or adjusted under 35 U.S.C. 154(b) by 34 days.

This patent is subject to a terminal disclaimer.

(21) Appl. No.: 11/958,500

(22) Filed: Dec. 18, 2007

(65) Prior Publication Data

US 2008/0161719 A1 Jul. 3, 2008

Related U.S. Application Data

(63) Continuation-in-part of application No. 11/157,569, filed on Jun. 21, 2005, now Pat. No. 7,309,317, and a continuation of application No. 10/159,692, filed on May 31, 2002, now Pat. No. 6,918,881.

(51) Int. Cl.
*A61B 10/00* (2006.01)
(52) U.S. Cl. .................................................... 600/567
(58) Field of Classification Search .......... 600/562–568
See application file for complete search history.

(56) References Cited

U.S. PATENT DOCUMENTS 5,121,751 A 6/1992 Panalletta
5,249,582 A * 10/1993 Taylor .......................... 600/567
6,918,881 B2 * 7/2005 Miller et al. .................. 600/567
7,309,317 B2 * 12/2007 Miller et al. .................. 600/567
2005/0203439 A1 9/2005 Heske et al.
2005/0234367 A1 10/2005 Miller et al.

FOREIGN PATENT DOCUMENTS

EP 1290978 A2 * 3/2003

OTHER PUBLICATIONS

International Search Report, PCT Patent Application PCT/US2008/081712, Dec. 24, 2008, 2 pages.

* cited by examiner

*Primary Examiner*—Max Hindenburg
*Assistant Examiner*—Brian Szmal
(74) *Attorney, Agent, or Firm*—Maginot Moore & Beck

(57) ABSTRACT

A biopsy needle assembly for use in a biopsy gun includes coaxially slidably engaged outer needle and inner needles. The inner needle defines a cavity adjacent its distal end for receiving a tissue sample. A first hub is attached to the proximal end of the inner needle, and a second hub is attached to the proximal end of the outer needle. An elongated pin having a first end and a second end is fixedly attached to the first hub at the first end of the pin. The second end is in sliding contact with the second hub so that the second hub and the pin are slidable relative to each other. A stop engagement is provided between the second end of the pin and the second hub and is configured to prevent disengagement of the outer and inner needles and to maintain a specific physical relationship between the hubs.

14 Claims, 10 Drawing Sheets

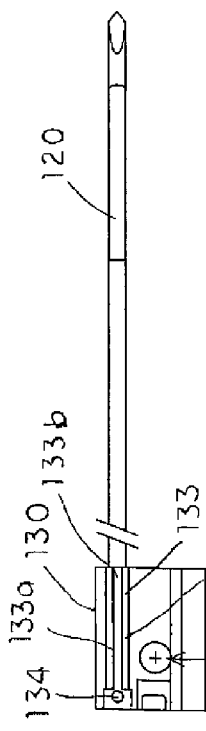
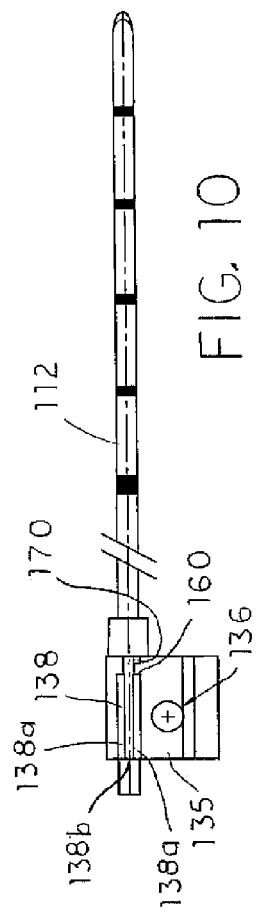
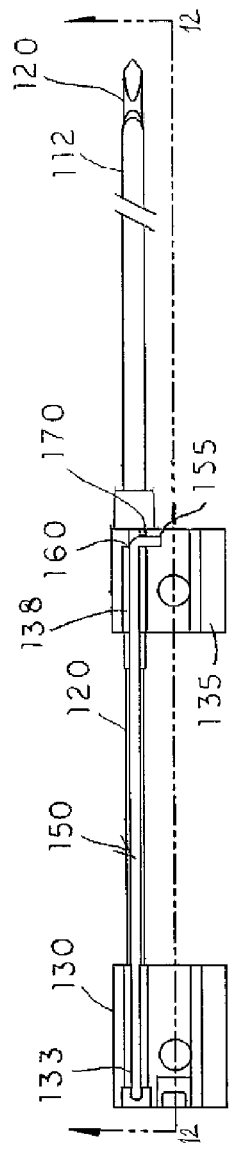
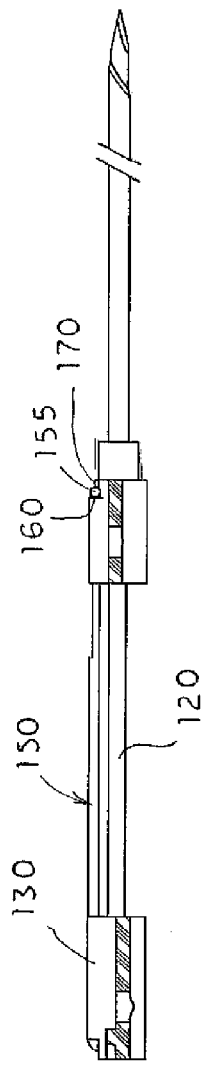
FIG. 9
FIG. 10
FIG. 11
FIG. 12

BIOPSY NEEDLE WITH INTEGRATED GUIDE PIN

REFERENCE TO RELATED APPLICATION

This application is a continuation-in-part to application Ser. No. 11/157,569, now issued as U.S. Pat. No. 7,309,317, which was filed on Jun. 21, 2005, and claims priority to application Ser. No. 10/159,692, filed on May 31, 2002, now issued as U.S. Pat. No. 6,918,881.

BACKGROUND

The present invention relates to an improved biopsy needle suited for use in a biopsy gun, or for use as a surgical instrument.

Biopsy needles, as part of a biopsy system, are generally used in the medical field to remove tissue, cells or fluids from a body for examination. Known biopsy needles have at least one inner needle (stylet) and an outer needle (cannula). The stylet has a point to enable insertion of the needle into a body, and a recess or notch located near its distal end for receiving a tissue sample. The cannula is displaceably guided on the stylet and has sharp cutting edges. Both the stylet and cannula have a connecting element on their proximal ends to enable connection of the needle to the slides of a biopsy gun. The connecting elements in known biopsy needles generally have included either flanges that cooperate with matching contact surfaces on the slides, or recesses that engage a rib located on a slide wherein both the slide and the rib run along the length of the biopsy needle.

Some prior art biopsy needles have the disadvantage that it is sometimes difficult to insert them into the biopsy gun under sterile conditions. Some prior art biopsy guns require a certain spacing between the connecting elements on the stylet and cannula in order for the biopsy needle to be inserted into the biopsy gun. However, this task of inserting the biopsy needle into the biopsy gun while the connecting elements are maintained in a fixed orientation is difficult because the stylet is generally freely displaceable in the cannula. Therefore, it is generally necessary to align the connecting elements of the biopsy needle, either manually or through use of a separate spacer, prior to insertion into a biopsy gun.

After the biopsy needle is inserted into a biopsy gun, if a spacer clip is used, it is generally necessary to remove the spacer in order to close the lid and operate the biopsy gun. Conventional spacer clips require the molding of a separate spacer. This requirement of a separate molding step adds an additional step in the manufacturing and packaging process thereby increasing the costs to produce the biopsy needle. Moreover, the use of a separate spacer clip may require undue handling of the needle in order to connect and disconnect the spacer clip. Furthermore, some conventional biopsy guns do not permit the option of inserting the needle into a biopsy gun in the uncocked position. By permitting a biopsy needle to be inserted in an uncocked biopsy gun, the proper operation of the needle is checked prior to the gun being fired by moving the inner needle and the outer needle relative to each other during the cocking process. An additional disadvantage of some conventional biopsy needles is that under some conditions, the individual connecting elements slip or rotate relative to the slides they are carried on when inserted in a biopsy gun.

While some prior integrated spacers have addressed many of these problems by fixing the relationship between the hubs and needles, it is believed that some of them achieve these benefits at the expense of creating drag on the hubs during firing. Since these prior integrated spacers require a tight friction fit with the hubs, movement of the hubs within the gun may be compromised. Therefore, a need remains for improved integrated spacers.

SUMMARY

The present invention includes a biopsy needle particularly suited for use in a biopsy gun. The invention includes an integrated guide pin and a stop engagement. The guide pin stop engagement prevents disengagement of the cannula and the stylet, facilitates needle alignment without the use of extrinsic devices and prevents rotation and other movement of the inner and outer needles relative to each other and the slides in a biopsy gun. Additionally, the integrated design of the needle allows the needle to be easily prepackaged in a sterile, disposable condition.

Other features and advantages of the present invention will become readily apparent from the following detailed description, the appended claims and the accompanying drawings. It is to be understood that both the foregoing general description and the following detailed description are exemplary and provided for purposes of explanation only, and are not restrictive of the invention, as claimed.

BRIEF DESCRIPTIONS OF DRAWINGS

FIG. 9 is a top view of the first hub of the biopsy needle assembly shown in FIG. 8

FIG. 10 is a top view of the second hub of the biopsy needle assembly shown in FIG. 8.

FIG. 11 is a top view of the biopsy needle assembly shown in FIG. 8 with the first and second hubs in a first extended position for loading into a biopsy gun of the type shown in FIG. 7.

FIG. 12 is a side cross-sectional view of the biopsy needle assembly shown in FIG. 11, taken along line 12-12 as viewed in the direction of the arrows.

DESCRIPTION OF THE EMBODIMENTS

Figure 1:
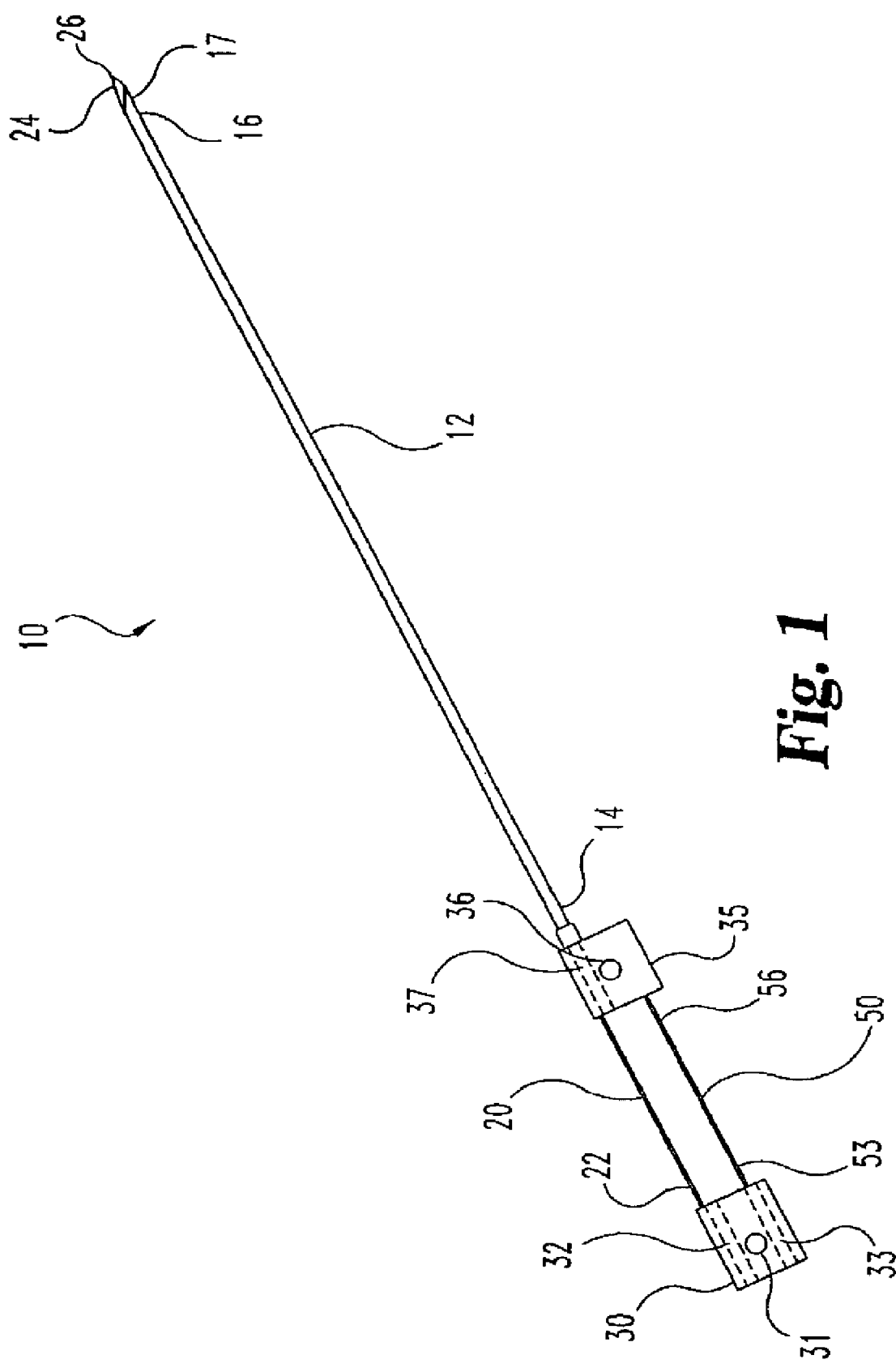
FIG. 1 is a side elevational view of a biopsy needle according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The present invention provides a biopsy needle having an integrated guide pin and a stop engagement. A preferred embodiment of a biopsy instrument 10 for use in a biopsy gun of this invention is shown schematically in FIG. 1. Instrument 10 includes a hollow outer needle 12 having a proximal end 14 and a distal end 16 and defining a lumen therethrough. An inner needle 20 is slidably engaged within the lumen. A first hub 30 is attached to the proximal end 22 of the inner needle. A second hub 35 is attached to the proximal end 14 of the outer needle 12.

The first hub 30 defines a longitudinally extending bore 32 for holding the proximal end 22 of inner needle 20. Bore 32 may extend through the entire length of the first hub 30; however it is not necessary so long as the proximal end 22 of inner needle is securely attached. Hub 30 also includes means for engaging the carriage of a biopsy device. In some embodiments, the means includes a vertically extending bore 31 as shown in FIG. 1. The second hub 35 may be identical to the first hub 30, except that the longitudinally extending bore 37 should extend through the entire length of the second hub 35. The longitudinally extending bore 37 of the second hub 35 holds the proximal end 14 of the outer needle 12. The second hub 35 further includes a second vertically extending bore 36 adapted to engage the carriage of a biopsy device.

For purposes of ease of manufacture, hubs 30, 35 may be identical. The hubs 30, 35 may be formed by insert molding and other techniques that are known in the art. According to one way of making the invention, the hubs 30, 35 are insert molded around inner needle 20 and outer needle 12, respectively. It should be noted that although the preferred embodiment illustrates vertically extending bores 31, 36 in the hubs 30, 35 for engagement to the slides of a biopsy gun, other configurations may be used, such as, for example, flanges.

Figure 2:
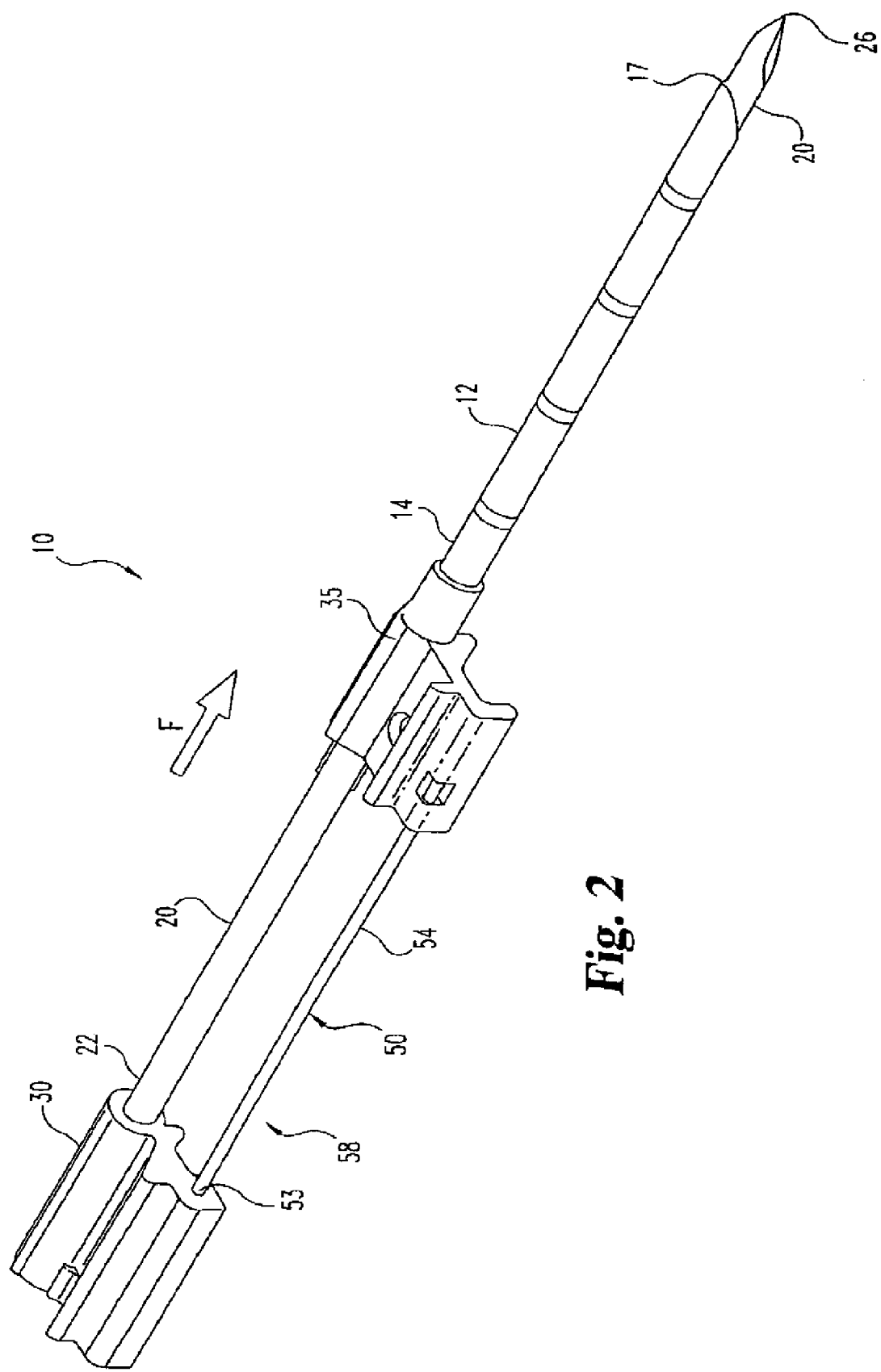
FIG. 2 is a top perspective view of a biopsy needle of this invention shown in the first position.
Figure 3:
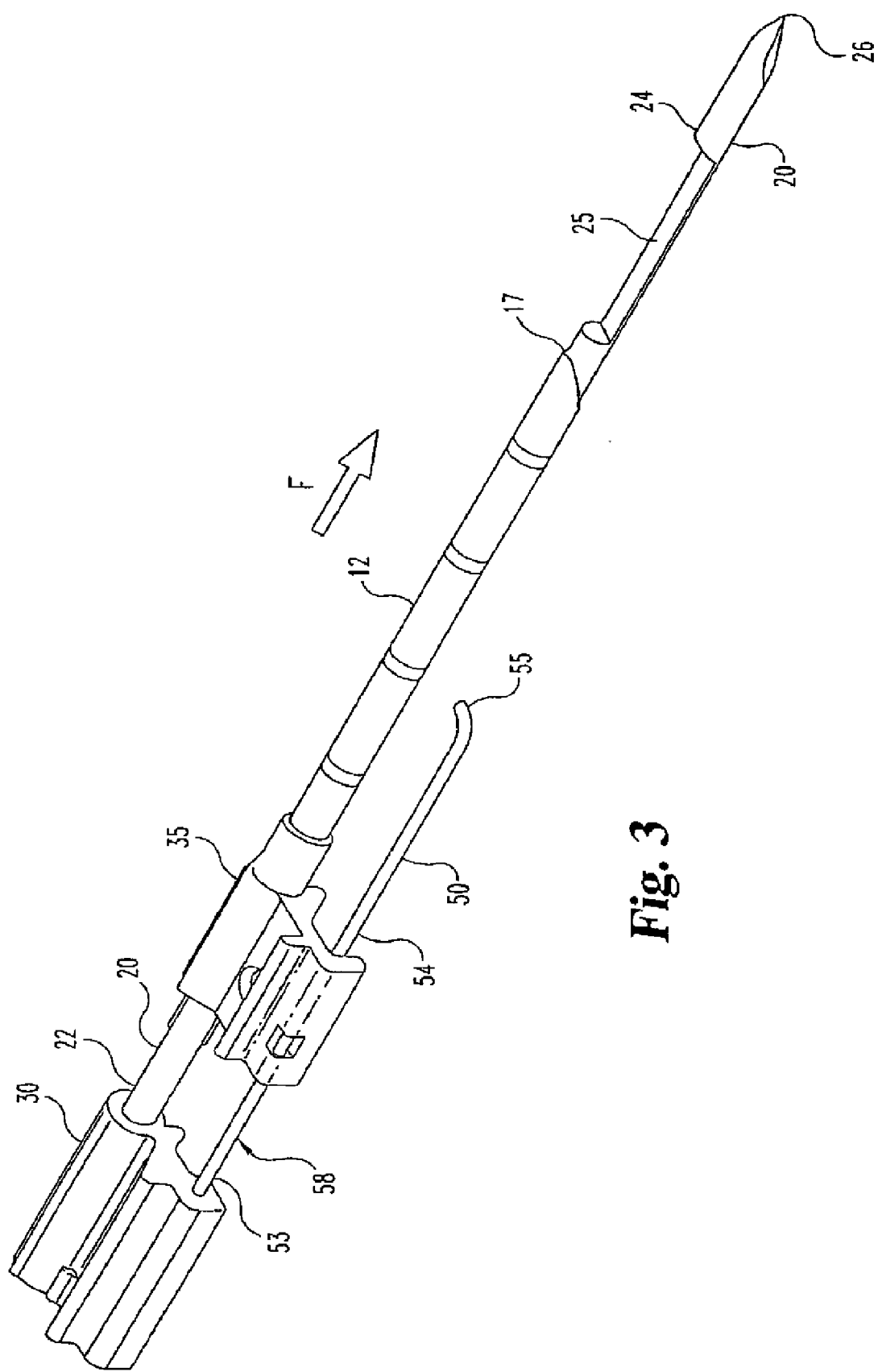
FIG. 3 is a top perspective view of the needle of FIG. 2 shown in the second position.

The hubs 30, 35 are moveable/slidable relative to one another between a first position shown in FIG. 2 wherein the distal end 24 of the inner needle 20 is retracted within the lumen and a second position shown in FIG. 3. In the second position, the distal end 24 of the inner needle 20 is extended away from the outer needle 12 to expose a cavity 25 defined adjacent the distal end 24 of the inner needle 20. In the first position, the cavity 25 is covered by the outer needle 12.

The design of the outer needle 12 and the inner needle 20 is generally well known in the art, and one or both may have a beveled cutting edge 17, 26 on their distal ends 16, 24, respectively. The inner needle 20 and the outer needle 12 may be of a variety of gauge sizes. The gauge and length of the inner needle and outer needle varies with the procedure for which it will be used. In particular embodiments, the needles are provided in lengths between 10 cm to 29 cm and gauge sizes of 20 gauge to 12 gauge.

An elongated pin 50 is provided to maintain proper relationships between the hubs 30, 35. The first end 53 of the pin 50 is fixedly attached to the first hub 30. In one particular embodiment, the first end 53 of the pin is engaged within a second longitudinal bore 33 defined through first hub 30 (FIG. 1). Second hub 35 and the pin 50 are slidable or moveable relative to each other, or in other words, second hub 35 is moveable relative to the pin 50 between the first and second ends 53, 56. The length of the pin may be configured to allow the biopsy needle 10 of the present invention to be used in various biopsy guns.

A stop engagement is provided between the second end 56 of the pin 50 and the second hub 35, which prevents disengagement of the outer and inner needles 12, 20. In some embodiments, the stop engagement involves an engagement member at the second end 56, which is configured to engage the second hub 35 when the second hub 35 is at the second end 56 of pin 50.

Referring now to FIGS. 2-5, details of one embodiment of the stop engagement are provided. In a specific embodiment, a track 38, which runs parallel to the outer needle 12, is provided on the second hub 35. The track 38 may be defined by the surface 41, a wall member 44 projecting from the surface 41 and a dog 46 projecting from the wall 44. Pin 50 is slidably disposed within track 38. The shaft 54 of pin 50 runs parallel to the needles 12, 20, and the second hub 35 is slidable along the pin 50 between a location 58 near the first end 53 and the second end 56.

In a specific embodiment, a stop member 60 projects from surface 41 of the second hub 35 adjacent the track 38. The engagement member engages the second hub 35 at the stop member 60. In this embodiment, the engagement member is an arm 55 projecting from the second end 56 of the pin 50. In a specific embodiment, arm 55 is formed from a bend in pin 50. However, any suitable means of creating arm 55 is contemplated.

Figure 4:
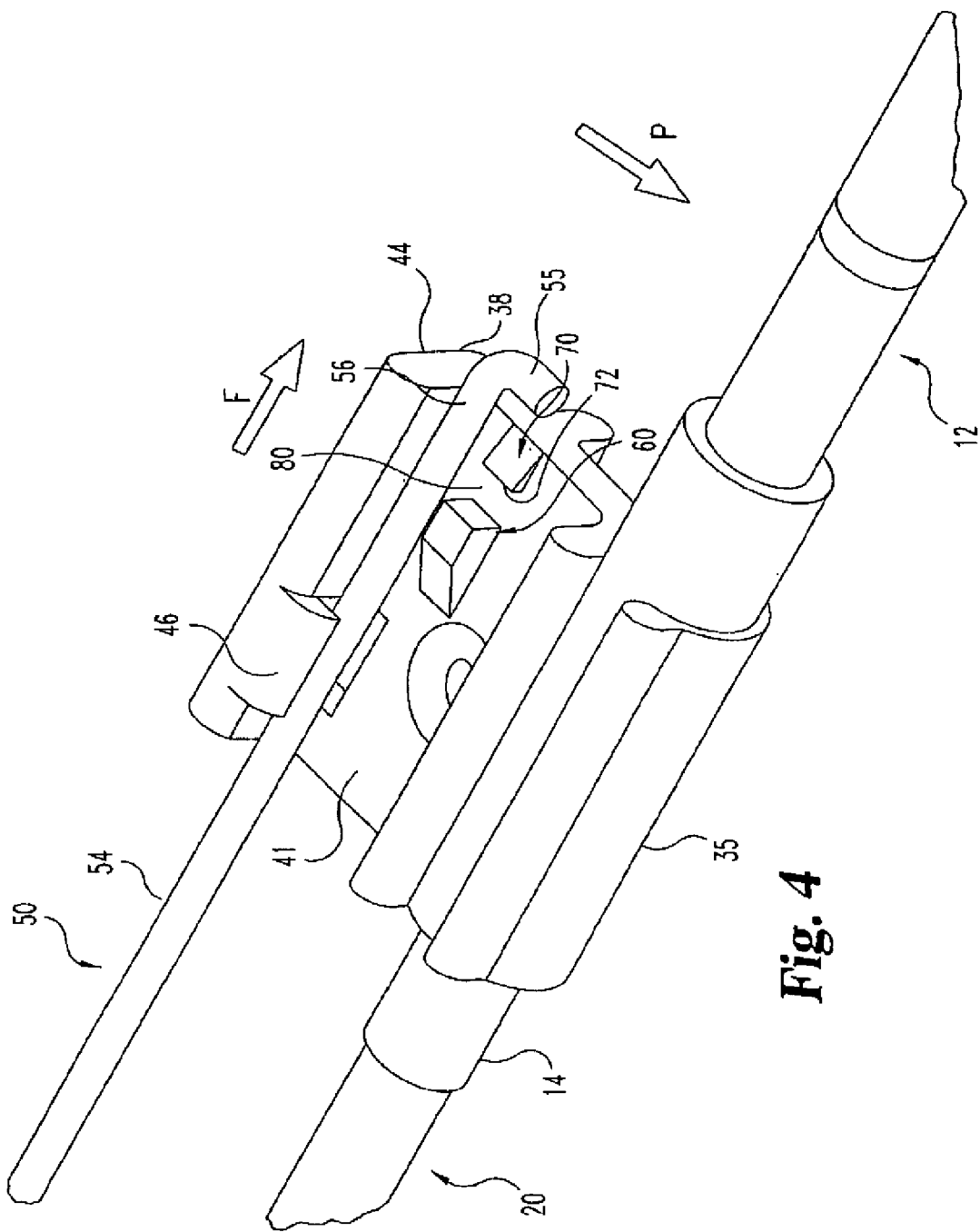
FIG. 4 is a partial bottom perspective view of the second hub of the needle of FIG. 2 shown approaching the second position.
Figure 5:
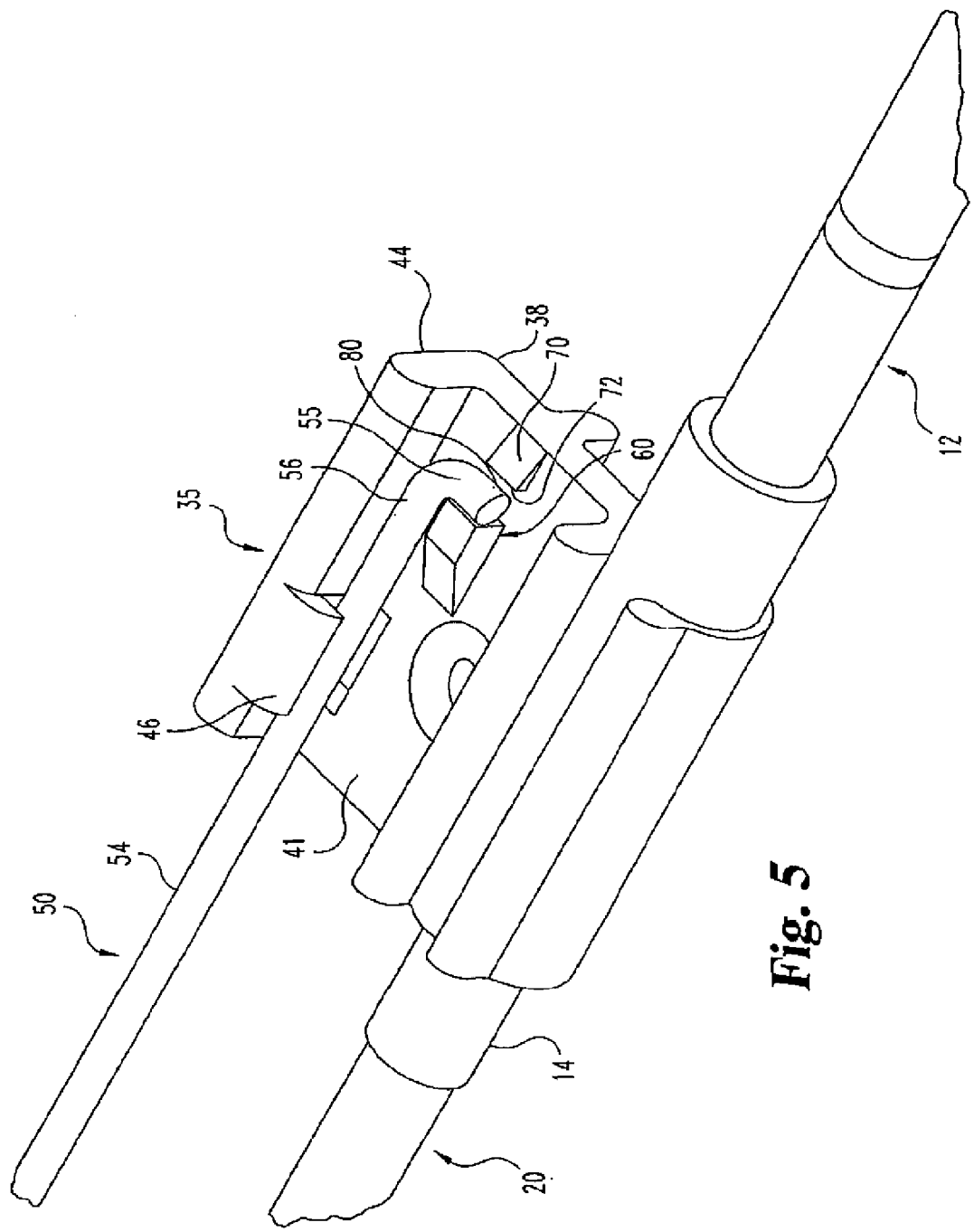
FIG. 5 is a partial bottom perspective view of the second hub of the needle of FIG. 2 shown in the second position.
Figure 6:
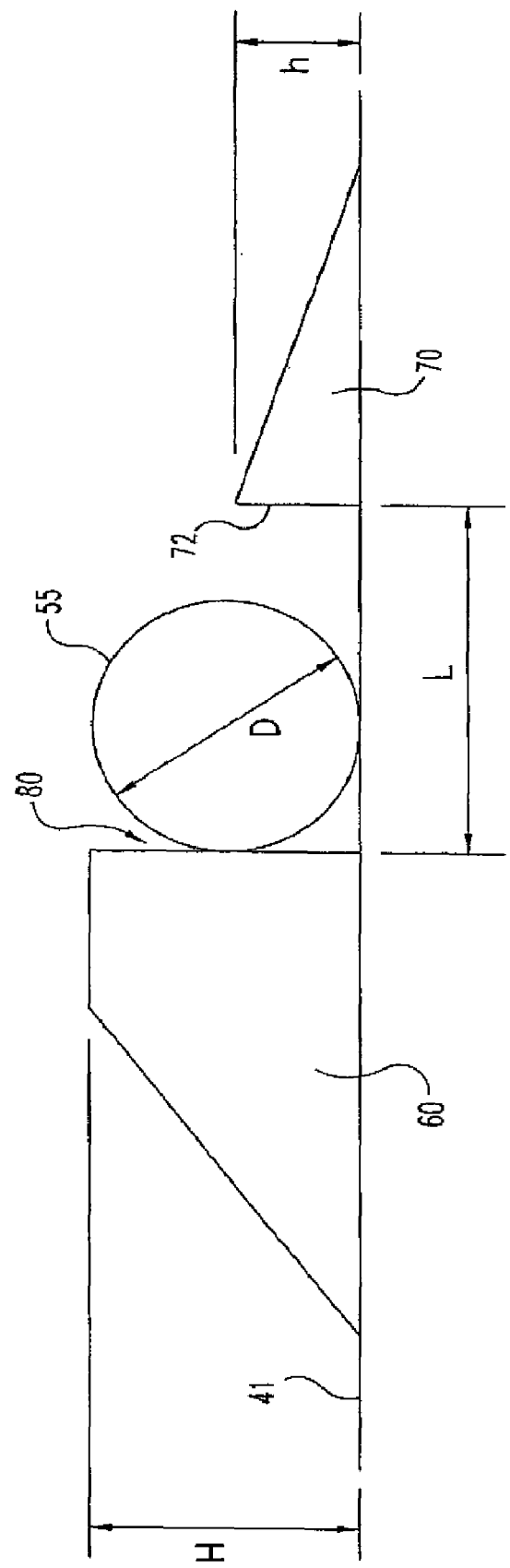
FIG. 6 is a side view of a portion of the second hub showing the relationship between the ramp and the stop member.

Referring now to FIGS. 4-6, the embodiment shown further includes a ramp 70 projecting from the surface 41 at a location distal to the stop member 60. Ramp 70 is inclined towards stop member 60. Ramp 70 includes a ramp head 72 facing stop member 60. The space 80 between ramp 72 and stop member 60 has a length L that is at least as large as a cross sectional dimension of said arm 55. In embodiments wherein arm 55 is tubular, the cross sectional dimension is the diameter D. Stop member 60 has a height H that is sufficient to prevent arm 55 to roll over stop member during operation of the device 10. Ramp has a height h sufficient to prevent the arm 55 from backing over the ramp 70 as the biopsy instrument 10 is inserted into the biopsy gun. In one specific embodiment, ramp 70 has a height h of at least about one third of the height of the arm 55. When arm 55 is tubular, the height will be the diameter D. In one specific embodiment, ramp 55 has a height D sufficient to provide a tactile indication when arm 55 slides over ramp 70 and into said space 80.

Some embodiments of the biopsy needle 10 of this invention provide several advantages over conventional biopsy needles and even those conventional biopsy needles that employ separate and integral spacer clips. When the biopsy needle 10 of the present invention is in the first position as shown in FIG. 5, the first and second hubs 30, 35 are in the maximally displaced position. With the arm 55 within space 80, the user may easily insert the biopsy needle 10 into the gun without moving the position of the hubs 30, 35 relative to each other. In this position, the distance between the vertical bores 31, 36 is sufficient to align these holes with posts located on the slides of a cocked biopsy gun. In addition the hubs, and therefore the needles, are kept in proper rotational alignment.

Therefore, biopsy needle 10 can be loaded into a biopsy gun without manipulation of the hubs 30, 35. Moreover, while some integrated spacer devices provide these same advantages, it is believed that some of them achieve these benefits at the expense of creating drag on the hubs during firing. Since these prior integrated spacers require a tight friction fit with the hubs, movement of the hubs within the gun may be compromised.

The biopsy needle 10 of this invention can be inserted into a biopsy gun either in the cocked or uncocked position to accommodate the user's preference. The pin 50 also facilitates removal of the biopsy needle 10 from a biopsy gun without the necessity to reattach a spacer clip as is required with some prior biopsy needles. If the biopsy needle 10 is inserted while the gun is uncocked, the gun should be cocked prior to use.

Figure 7:
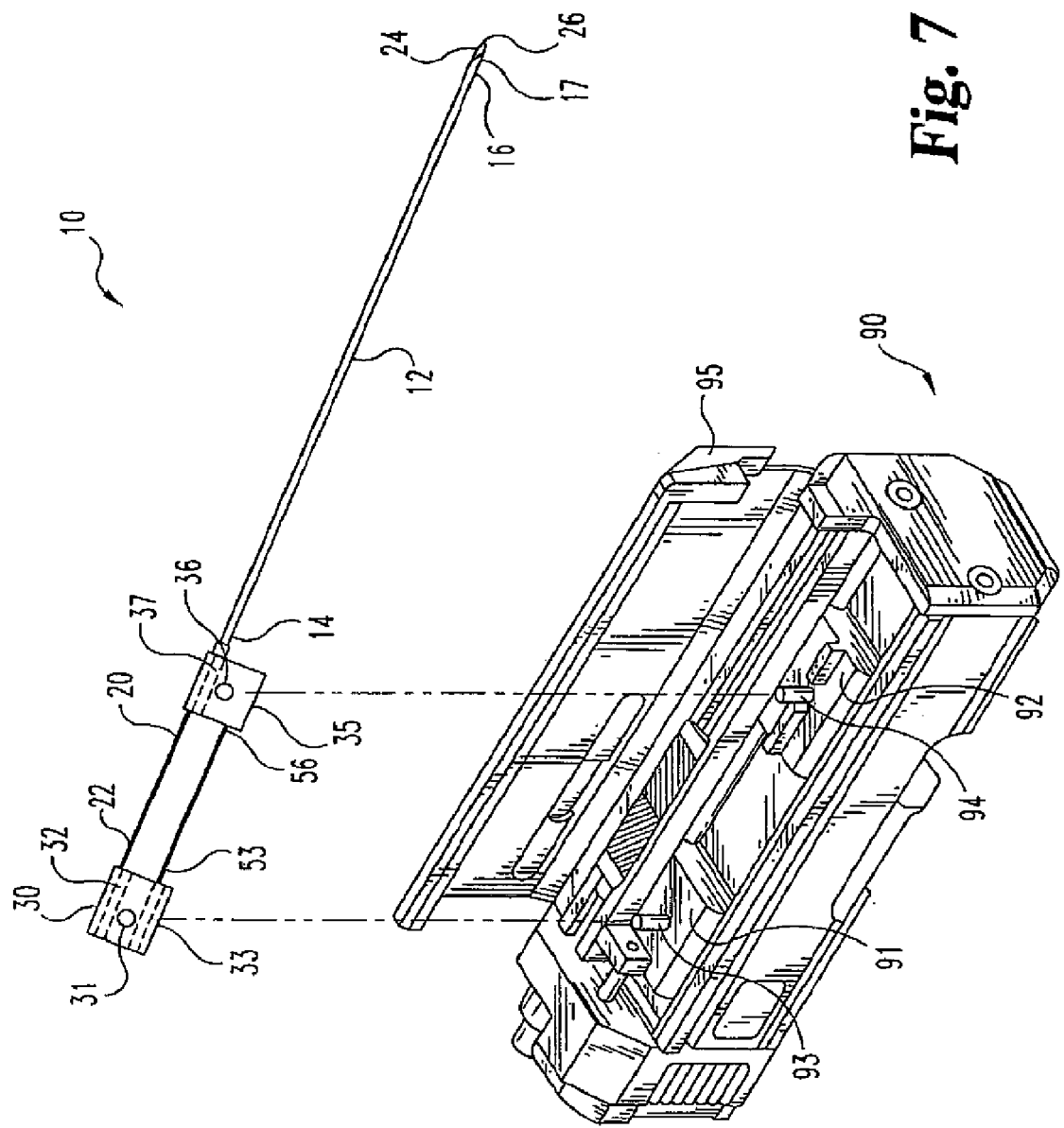
FIG. 7 is an isometric view of one embodiment of the biopsy needle of the present invention used in conjunction with a biopsy gun of a type that is well-known in the art.

The device 10 can be shipped in the second position (FIG. 3) with the hubs 30, 35 close together. Insertion of the biopsy needle 10 into a biopsy gun 90 is generally straight forward as shown in FIGS. 4, 5 and 7. The user moves the second hub 35 away from the first hub 30 towards the distal end 16, which moves the outer needle 12 to cover the cavity 25 of inner needle 20. As the second hub 35 travels forward in the direction of arrow F in FIG. 4, arm 55 encounters the ramp 70 and travels over the incline and into the space 80 and contacts the stop member 60. At this point, the user feels a definite click. This tactile indicator tells the user that the device is in position to be loaded.

The device is now in the first position shown in FIG. 2. The outer needle 12 is positioned over cavity 25, the beveled tip 26 of inner needle 20 is exposed, and the rotational relationship of the hubs and, as a result, the needle cavity and beveled tips, is fixed. When the first and second hubs 30, 35 are maximally displaced relative to each other in the first position, the distance between the bore 31 in the first hub 30 and the bore 36 in the second hub 35 is such that the biopsy needle 10 can be inserted with the proper spacing into a biopsy gun in the cocked position as shown in FIG. 7. The hubs 30, 35 are also in proper orientation for operation of the gun 90. This eliminates the need for any external means of achieving the proper spacing of the needle. Alternatively, the needle can be mounted in a biopsy gun in the uncocked position.

One of the hubs is grasped by the user and placed over the interior chamber of the biopsy gun 90, as illustrated in FIG. 7. Vertically extending bores 31, 36 of the first and second hubs 30, 35 are aligned over the slides 91, 92 of the biopsy gun 90 and receive posts 93, 94, respectively. Without having to remove the integrated pin 50, the lid 95 to the biopsy gun 90 is closed and is ready for use.

In some embodiments, the tip 26 of inner needle 20 is exposed to facilitate insertion of the biopsy needle 10 into the tissue being sampled. After tip 26 is properly positioned within the tissue, the biopsy gun is then triggered causing the first hub 30 and the pin 50 to move forward towards the distal end in the direction of arrow F, while the second hub 35 is held stationary. This movement causes the inner needle 20 to move forward into the tissue being sampled and exposes the cavity 25, which receives the tissue to be sampled. The device is now in the second position depicted in FIG. 3. For the pin 50 to move, the arm 55 must overcome the ramp head 72 to move out of space 80. While the arm 55 will not back out over the ramp 70 during loading of the gun 90, the force of the gun 90 is more than sufficient to smoothly overcome the ramp head 72 without interfering with the action of the gun 90.

The second slide 92 of the biopsy gun 90 is then triggered moving the second hub 35 forward in the direction of arrow F. This action causes the outer needle 12 to move forward over cavity 25, which causes outer needle 12 to separate and trap tissue prolapsed in the cavity 25. At this point, the device 10 has returned to the first position shown in FIG. 2 with the arm 55 in the space 80 (FIG. 5). The biopsy needle 10 can then be removed and the tissue examined. The pin 50 in engagement with the first and second hubs 30, 35 during operation of the biopsy gun 90, stabilizes the first and second hubs 30, 35 and prevents twisting and bending in the biopsy gun 90. The hubs 30, 35 are fixed rotationally relative to one another due to the fixed connection of the first end 53 of the pin 50 within the longitudinal bore 33 of the first hub 30 and the cooperation of the longitudinal bore 33, the track 38, and the dog 46 to prevent rotation of the hubs 30, 35 relative to each other.

Figure 8:
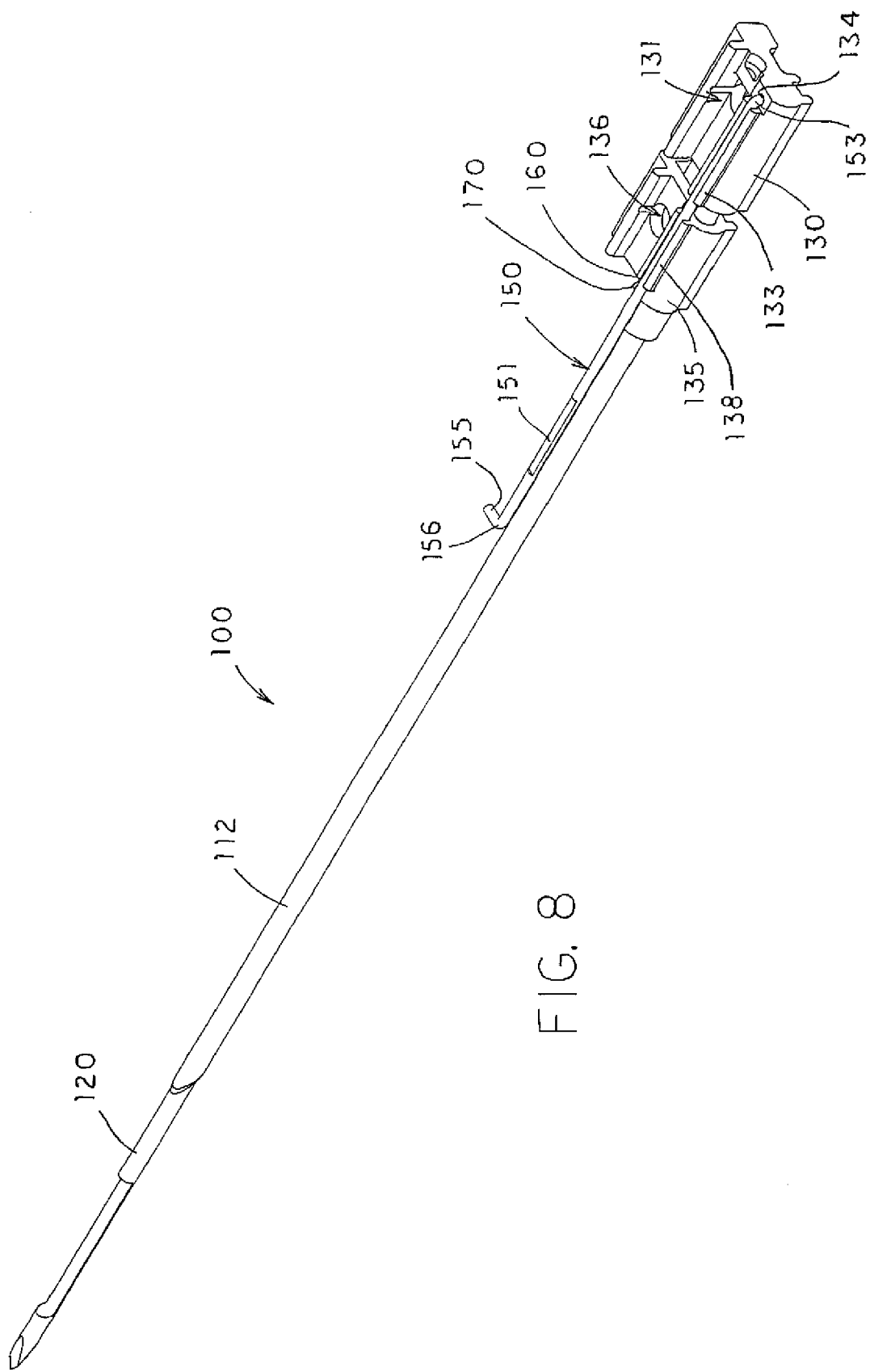
FIG. 8 is a top perspective view of another embodiment of a biopsy needle assembly with the first and second hubs in a second closed position.

In another embodiment of the invention, the integrated guide pin and stop components are arranged in a "stacked" configuration in which the guide pin is positioned directly above the axis of the needles. Thus, a biopsy needle assembly 100, shown in FIG. 8, includes an outer needle 112 and an inner needle 120 that may be configured similar to the needles 12 and 20 described above. The inner needle 120 is fixed to a first rearmost hub 130, while the outer needle 112 is fixed to a second forward hub 135, again in a manner similar to that described above. Both hubs include carriage engagement features 131, 136, respectively that are configured to allow the biopsy needle assembly 100 to be mounted within a biopsy gun, such as the gun depicted in FIG. 7.

In this embodiment, the guide pin 150 is oriented above the inner needle 120 extending from the first hub 130, as best seen in FIGS. 11, 12. The first hub thus includes an elongated track 133 sized to receive the pin 150 therein, as illustrated in FIG. 9. The hub 130 further defines a bore 134 at one end of the track to receive the bent first end 153 of the pin. In one specific embodiment, the walls 133a of the track 133 can be configured to form a snap-fit engagement about the pin to firmly hold the pin 150 to the first hub 130. The track defines a channel 133b between the walls that can fit snugly about the pin.

The second hub 135 also defines a second track 138 directly above the engagement between the outer needle 112 and the hub 135, as shown in FIG. 10. The second track 138 is configured to allow the pin 150 to slide within the track as the biopsy needle activation propels the first hub forward toward the second hub, as described above. In a specific embodiment, the walls 138a of the track 138 may be configured for a snap-fit engagement, but with sufficient clearance in the channel 133b for the pin to slide smoothly therein.

Like the pin 50, the pin 150 includes an arm 155 at the second end 156 of the pin. This arm is configured to engage a stop and ramp defined on the second hub 135 in a manner similar to that described above with respect to pin 50. In this embodiment, the stop surface 160 is defined by the end of the track 138, as illustrated in FIG. 10. Offset from this stop surface 160 is a projection or ramp element 170. The projection has a height from the body of the hub 135 that is sufficient to retain the arm 155 of the pin between the projection and the stop surface, such as when the two hubs are in their extended position shown in FIGS. 11, 12. The projection 170 must further have a height that can be easily traversed by the arm 155 of the pin when the hubs are activated by the biopsy needle carriage mechanisms. Consequently, the projection or ramp element 170 may have the same dimensional relationship to the arm 155 of the pin 150 as between the ramp 70 and pin 50 described above in connection with FIG. 6. The element 170 may further incorporate a ramp head similar to the ramp head 72 and a beveled surface similar to that shown in FIG. 6.

In the illustrated embodiment, one ramp 170 is provided off to one side of the track 138. The position of the ramp is dictated by the direction at which the arm 155 of the pin 150 is bent. It is of course contemplated that an arm 155 that is 180° offset from the position shown in the figures would necessitate that the ramp 170 be positioned on the opposite side the track from what is illustrated. Alternatively, a ramp may be provided on both sides of the track. In yet another alternative, the end 156 of the pin 150 may be configured as a "T", with arms 155 projecting toward both sides.

In certain embodiments, the pin 150 may include a notch 151 formed adjacent the second end 156 and arm 155. The notch 151 provides a region of reduces cross-sectional area adjacent the free end of the pin.

The arrangement of the tracks 133 and 138 and the pin 150 help maintain the hubs 130, 135 in alignment within a common plane when the hubs are in their extended position depicted in FIGS. 11, 12. The pin also helps hold the angular orientation between the hubs in that extended position.

Other embodiments of the invention will be apparent to those skilled in the art from consideration of the specification and practice of the invention disclosed herein. For example, in another embodiment, arm 55 engages another portion of the second hub 35, such as wall member 48. In this embodiment, pin 50 is rotated 180°, and the stop member 60 is not required.

Figure 13:
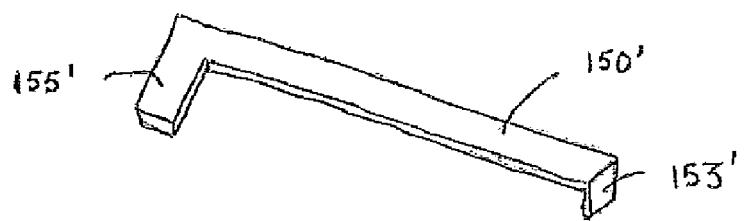
FIG. 13 is a top perspective view of the elongated pin as a flat wire.

In both embodiments, the pins 50, 150 are shown as a cylindrical wire. However, in alternative embodiments, a pin 150' may be formed of flat wire as shown in FIG. 13, with appropriate modifications to the tracks for sliding contact with the respective pins. Like the pins 50 and 150, pin 150' includes an arm 155' and a bent first end 153' that have the same dimensional relationship as the arm and bent end in the other embodiments described above.

Moreover, in both embodiments, the pins 50, 150 are shown anchored to the first hub 30, 130, respectively. However, in alternative embodiments, the first ends 53, 153 of the respective pins may be anchored to the corresponding second hub 35, 135, with the pins extending rearward toward the first hub 30, 130. In this alternative, the ramp and stop components would be formed on the first hub, rather than on the second hub.

In the illustrated embodiments, the ramp element 70 presents beveled configuration that the arm 55 of the pin rides up as the two hubs are moved to their extended positions. Alternatively, the beveled ramp feature may be incorporated into the arm to allow the arm to ride up the element 70, which may or may not be similarly beveled.

It is intended that the specification, drawings and examples be considered as exemplary only, with the true scope and spirit of the invention being indicated by the following claims. It should be understood that only the preferred embodiments have been shown and described and that all changes and modifications that come within the spirit of the invention are desired to be protected.

What is claimed:

1. A biopsy needle assembly for use in a biopsy gun, comprising:
    a hollow outer needle having a proximal end and a distal end and defining a lumen therethrough, said outer needle defining an axis along the length of the needle;
    an inner needle slidably disposed within said lumen, said inner needle having a proximal end and a distal end and defining a cavity adjacent said distal end for receiving a tissue sample;
    a first hub having a length and attached to said proximal end of said inner needle along said axis;
    a second hub having a length and attached to said proximal end of said outer needle along said axis;
    one of said first and second hubs including:
        a lower surface and an upper surface;
        a first elongated track defined on said upper surface directly above said axis; said elongated track defining a first channel parallel to said axis and a stop surface at one end of said track; said first channel extending substantially along said length of said one of said first and second hubs; and
        a projection spaced apart from said stop surface to define a space therebetween, said space having a length; and
    an elongated pin having a first end, a second end and an arm projecting from said second end, said arm having a cross sectional dimension slightly less than said length, said pin slidingly disposed within said first channel of said one of said first and second hubs, and said first end of said pin connected to the other of said first and second hubs to move therewith, said one of said first and second hubs and said pin being slidable relative to each other between a position in which said arm is positioned in said space and a position in which said arm is outside said space.

2. The biopsy needle assembly of claim 1, wherein said pin has a length sufficient that when said arm is positioned in said space said first and second hubs are spaced a predetermined distance to enable insertion of said biopsy needle in a biopsy gun.

3. The biopsy needle assembly of claim 1, wherein said projection is a ramp inclined toward said stop surface.

4. The biopsy needle assembly of claim 1, wherein said projection is sized relative to said arm of said elongated pin to resist but not prevent dislodgement of said arm from within said space by axial movement of one hub relative to the other.

5. The biopsy needle assembly of claim 4, wherein said projection has a height of at least about one third of a height of said arm.

6. The biopsy needle assembly of claim 4, wherein said ramp has a height sufficient to provide a tactile indication when said arm slides over ramp and into said space.

7. The biopsy needle assembly of claim 1, wherein said elongated pin has a circular cross-section.

8. The biopsy needle assembly of claim 1, wherein said first track is defined by opposing walls, an end of at least one of said walls forming said stop surface.

9. A biopsy needle assembly for use in a biopsy gun, comprising:
    a hollow outer needle having a proximal end and a distal end and defining a lumen therethrough, said outer needle defining an axis along the length of the needle;
    an inner needle slidably disposed within said lumen, said inner needle having a proximal end and a distal end and defining a cavity adjacent said distal end for receiving a tissue sample;
    a first hub attached to said proximal end of said inner needle along said axis;
    a second hub attached to said proximal end of said outer needle along said axis;
    one of said first and second hubs including:
        a first elongated track defining a first channel parallel to said axis and a stop surface at one end of said track; and
        a projection spaced apart from said stop surface to define a space therebetween, said space having a length; and
    an elongated pin having a first end, a second end and an arm projecting from said second end, said arm having a cross sectional dimension slightly less than said length, said pin slidingly disposed within said first channel of said one of said first and second hubs, and said first end of said pin connected to the other of said first and second hubs to move therewith, said one of said first and second hubs and said pin being slidable relative to each other between a position in which said arm is positioned in said space and a position in which said arm is outside said space; and said elongated pin is disposed within said first track in a snap-fit engagement.

10. A biopsy needle assembly for use in a biopsy gun, comprising:
    a hollow outer needle having a proximal end and a distal end and defining a lumen therethrough, said outer needle defining an axis along the length of the needle;
    an inner needle slidably disposed within said lumen, said inner needle having a proximal end and a distal end and defining a cavity adjacent said distal end for receiving a tissue sample;
    a first hub attached to said proximal end of said inner needle along said axis;
    a second hub attached to said proximal end of said outer needle along said axis;
    one of said first and second hubs including:
        a first elongated track defining a first channel parallel to said axis and a stop surface at one end of said track; and
        a projection spaced apart from said stop surface to define a space therebetween, said space having a length;
    an elongated pin having a first end, a second end and an arm projecting from said second end, said arm having a cross sectional dimension slightly less than said length, said pin slidingly disposed within said first channel of said one of said first and second hubs, and said first end of said pin connected to the other of said first and second hubs to move therewith, said one of said first and second hubs and said pin being slidable relative to each other between a position in which said arm is positioned in said space and a position in which said arm is outside said space;

wherein said other of said first and second hubs includes a second elongated track defining a second channel coaxial with said first channel and sized to receive said elongated pin therein.

11. The biopsy needle assembly of claim 10, wherein said elongated pin is disposed within said second elongated track in a snap-fit engagement.

12. The biopsy needle assembly of claim 11, wherein said second channel and said elongated pin are sized for a snug fit.

13. A biopsy needle assembly for use in a biopsy gun, comprising:

a hollow outer needle having a proximal end and a distal end and defining a lumen therethrough, said outer needle defining an axis along the length of the needle;

an inner needle slidably disposed within said lumen, said inner needle having a proximal end and a distal end and defining a cavity adjacent said distal end for receiving a tissue sample;

a first hub attached to said proximal end of said inner needle along said axis;

a second hub attached to said proximal end of said outer needle along said axis;

one of said first and second hubs including:

a first elongated track defining a first channel parallel to said axis and a stop surface at one end of said track; and a projection spaced apart from said stop surface to define a space therebetween, said space having a length;

an elongated pin having a first end, a second end and an arm projecting from said second end, said arm having a cross sectional dimension slightly less than said length, said pin slidingly disposed within said first channel of said one of said first and second hubs, and said first end of said pin connected to the other of said first and second hubs to move therewith, said one of said first and second hubs and said pin being slidable relative to each other between a position in which said arm is positioned in said space and a position in which said arm is outside said space;

wherein said elongated pin includes a bend at said first end; and said other of said first and second hubs defines a bore to receive said bend of said pin to connect said pin thereto.

14. A biopsy needle assembly for use in a biopsy gun, comprising:

a hollow outer needle having a proximal end and a distal end and defining a lumen therethrough, said outer needle defining an axis along the length of the needle;

an inner needle slidably disposed within said lumen, said inner needle having a proximal end and a distal end and defining a cavity adjacent said distal end for receiving a tissue sample;

a first hub attached to said proximal end of said inner needle along said axis;

a second hub attached to said proximal end of said outer needle along said axis;

one of said first and second hubs including:

a first elongated track defining a first channel parallel to said axis and a stop surface at one end of said track; and a projection spaced apart from said stop surface to define a space therebetween, said space having a length; and a flat wire having a first end, a second end and an arm projecting from said second end, said arm having a cross sectional dimension slightly less than said length, said flat wire slidingly disposed within said first channel of said one of said first and second hubs, and said first end of said flat wire connected to the other of said first and second hubs to move therewith, said one of said first and second hubs and said flat wire being slidable relative to each other between a position in which said arm is positioned in said space and a position in which said arm is outside said space.

* * * * *